United States Patent
Dimagno

(10) Patent No.: US 12,377,154 B2
(45) Date of Patent: *Aug. 5, 2025

(54) DRUG DELIVERY SYSTEM FOR TREATING DISEASE

(71) Applicant: SDG LLC, Cambridge, MA (US)

(72) Inventor: Stephen Dimagno, Chicago, IL (US)

(73) Assignee: SDG, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/303,387

(22) Filed: Apr. 19, 2023

(65) Prior Publication Data

US 2023/0381326 A1 Nov. 30, 2023

Related U.S. Application Data

(62) Division of application No. 16/759,793, filed as application No. PCT/US2018/058758 on Nov. 1, 2018, now Pat. No. 11,666,654.

(60) Provisional application No. 62/581,405, filed on Nov. 3, 2017.

(51) Int. Cl.
*A61K 47/58* (2017.01)
*A61K 31/519* (2006.01)
*C08F 220/58* (2006.01)

(52) U.S. Cl.
CPC ............ *A61K 47/58* (2017.08); *A61K 31/519* (2013.01); *C08F 220/58* (2013.01)

(58) Field of Classification Search
CPC ...... A61K 31/519; A61K 47/58; C08F 220/58
See application file for complete search history.

(56) References Cited

U.S. PATENT DOCUMENTS 11,666,654 B2  6/2023  Dimagno
2014/0357557 A1  12/2014  Cole et al.

FOREIGN PATENT DOCUMENTS

WO  WO 2004/077511 A2  9/2004
WO  WO 2015/187596 A2  12/2015

OTHER PUBLICATIONS

Gao et al., "Colon-specific 9-aminocamptothecin-HPMA copolymer conjugates containing a 1,6-elimination spacer", *Journal of Controlled Release* 110(2):323-331 (2006).
Huang et al., "PEG as a spacer arm markedly increases the immunogenicity of meningococcal group Y polysaccharide conjugate vaccine", *Journal of Controlled Release* 172:382-389 (2013).
International Search Report for International Application No. PCT/US2018/58758, mailed Jan. 15, 2009, 2 pages.
Tappertzhofen et al., "Bioreducible Poly-$_L$-Lysine-Poly[HPMA] Block Copolymers Obtained by RAFT-Polymerization as Efficient Polyplex-Transfection Reagents", *Macromolecular Bioscience* 16(1):106-120 (2016).
Yang et al., "Design of smart HPMA copolymer-based nanomedicines", *Journal of Controlled Release* 240:9-23 (2015).
Zhang et al., "Purification of Synthetic Peptides Using a Catching Full-Length Sequence by Polymerization Approach", *Organic Letters* 16(5):1290-1293 (2014).

*Primary Examiner* — Jianfeng Song
(74) *Attorney, Agent, or Firm* — Dechert LLP

(57) ABSTRACT

The present invention relates to HPMA-CBz copolymers and methods for treating certain diseases comprising administering the copolymers to a subject in need thereof.

18 Claims, No Drawings

DRUG DELIVERY SYSTEM FOR TREATING DISEASE

RELATED APPLICATIONS

This application is a divisional of U.S. patent application Ser. No. 16/759,793, filed on Apr. 28, 2020, which is a 35 U.S.C. § 371 national stage entry of international application No. PCT/US2018/058758, filed Nov. 1, 2018, which claims priority to U.S. Provisional application No. 62/581,405, filed on Nov. 3, 2017. Each of the above-referenced applications is herein incorporated by reference in their entirety.

FIELD

The invention relates generally to biotechnology and more particularly to polymeric delivery systems for the treating disease, including inflammatory diseases such as rheumatoid arthritis. The polymeric constructs include N-(2-hydroxypropyl)methacrylamide (HPMA) benzyl carbamate (Cbz) copolymer conjugates.

BACKGROUND

One method for decreasing the systemic toxicity of drug molecules is to develop targeted drug delivery vehicles capable of releasing the drug preferentially at the site of disease. For treating rheumatoid arthritis, (RA), this means that one should target the joints and synovial fluid to release an anti-inflammatory drug selectively. Attempts to effect this selective targeting can include using polymer-based compositions that releases the drug selectively in the joints, thus averting some of the systemic effects of some drugs, such as steroid toxicity. For poly(N-(2-hydroxypropyl) methacrylamide "HPMA")-dexamethasone delivery systems ("P-Dex", see, e.g., US 20080159959 and US 20090311182), the targeting selectivity is a property of the polymer itself; pHPMA accumulates selectively in the joint tissue. This delivery technology additionally uses a pH sensitive hydrazone linkage in which the rate of release increases with an increase in hydrogen ion concentration (at lower pH). Because the pH of the synovial fluid in rheumatoid arthritis patients is generally lower than that of the blood, the acid sensitive drug release mechanism enhances the targeting selectivity inherent in the polymer and allows for the controlled, local administration of dexamethasone at high local, and low systemic doses.

Unfortunately, the hydrazine linking strategy is only compatible with drugs that can form hydrazones—that is, drugs that possess a ketone or aldehyde functionality. Many drugs, including many anti-arthritic compounds, do not have these functional groups. Thus, they can neither be appended to HPMA nor benefit from the increased targeting and reduced toxicity possible with the pHPMA drug delivery system. Therefore, a need exists for developing delivery systems that do not require a ketone or aldehyde functionality.

SUMMARY

The invention provides HPMA-based delivery systems in which the HPMA monomer is linked to a benzyl carbamate group (CBz). The presence of the Cbz group in the HPMA monomer allows for attachment of agents, such as drugs, that lack a ketone or aldehyde functionality. The Cbz linker strategy thus dramatically expands the number of compounds that can be incorporated into pHPMA constructs. In embodiments, the new monomers feature a readily cleavable, acid sensitive benzyl carbamate group.

Suitable drugs that can be used in the compositions and methods disclosed herein include, e.g., javelin kinase inhibitors, e.g., baricitinib, ruxolitinib, tofacitinib, oclacitinib, upadacitinib, and/or peficitinib.

In one aspect the invention features a composition comprising an N-(2-hydroxypropyl)methacrylamide-benzyl carbamate (HPMA-Cbz) monomer.

In embodiments, the HPMA-Cbz monomer is synthesized from one or more acid-labile, CBz derived linkers.

The linker can be an activated linker.

In some embodiment, the composition further includes a therapeutic agent or drug, e.g., a a janus kinase inhibitor. A janus kinase inhibitor can be, e.g., baricitinib, tofacitinib, oclacitinib, upadacitinib, and/or peficitinib.

In an embodiment, the inhibitor is baricitinib.

In another aspect, the invention provides a method of synthesizing a polymer by copolymerizing a HPMA-Cbz monomer under conditions sufficient to form the polymer. The polymer may be formed by an HPMA-Cbz monomer in the presence of a therapeutic agent or drug, or in the absence of the drug.

In another aspect the invention provides a co-polymer of HPMA and HPMA-Cbz-Drug.

In embodiments, the copolymer has one of the following structures:

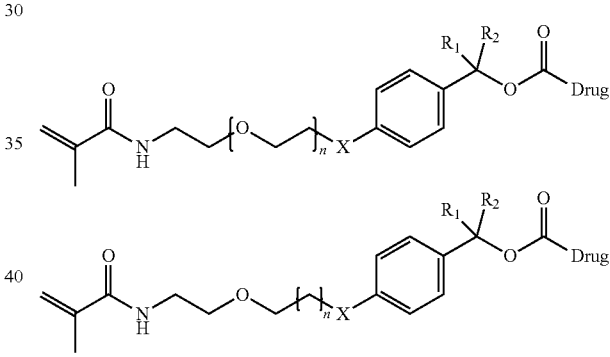

wherein X is CH2, NH, N—$R_3$, O, S; n=0-8, $R_1$=alkyl, $R_2$=alkyl, $R_3$=acetyl or $CH_3$.

In various embodiments, the polymer has a polydispersity index (PDI) PDI between 1.1 and 1.6, e.g., 1.2 to 1.6, 1.3 to 1.5, or 1.4.

In various embodiments, the polymer is 0.1%-50% HPMA-CBz monomer, e.g., 0.2, 0.5, 1.0. 1.5, 2.0, 3.0, 5, 7.5, 10, 15, 20, 25, 30, 35, 40, 45, or 48% HPMA-CBz.

In various embodiments the molecular weight of the polymer is 1,000 to 100,000 daltons, e.g., 2,000 to 90,000 daltons, 3,000 to 80,000 daltons, 10,000 to 60,000 daltons, to 55,000 daltons, or 20,000 to 40,000 daltons.

Among the advantages of this new linking strategy is that drug molecules featuring primary or secondary amine groups may be incorporated into the pHPMA drug delivery system, thereby lifting the requirement that the released drug contain a ketone or aldehyde.

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of the steps or features.

DETAILED DESCRIPTION

The invention provides polymers of HPMA-Cbz-therapeutic agents. For convenience, before further description of the present invention, certain terms used in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art. The terms used throughout this specification are defined as follows, unless otherwise limited in specific instances.

The articles "a," "an" and "the" are used to refer to one or to more than one (i.e., to at least one) of the grammatical object of the article.

The terms "comprise" "comprising" "including" "containing" "characterized by" and grammatical equivalents thereof are used in the inclusive, open sense, meaning that additional elements may be included. It is not intended to be construed as "consists of only."

As used herein, "consisting of" and grammatical equivalent thereof exclude any element, step or ingredient not specified in the claim.

As used herein, the term "about" or "approximately" usually means within 20%, more preferably within 10%, and most preferably still within 5% of a given value or range.

The term "biodegradable" as used herein refers to both enzymatic and non-enzymatic breakdown or degradation of the polymeric structure.

Making HPMA-Cbz Monomers and Polymers

HPMA-Cbz monomers can be synthesized using the synthetic schemes described in the Examples and as shown below:

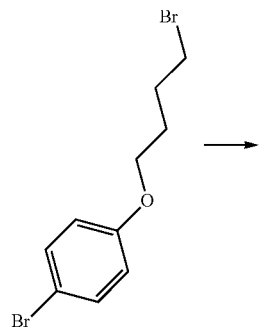

I

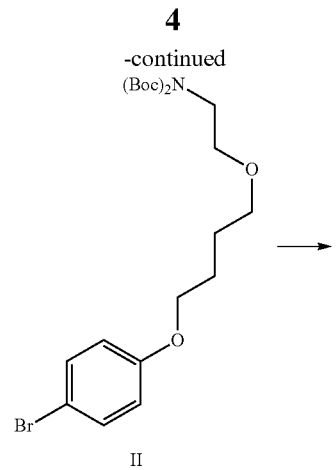

II

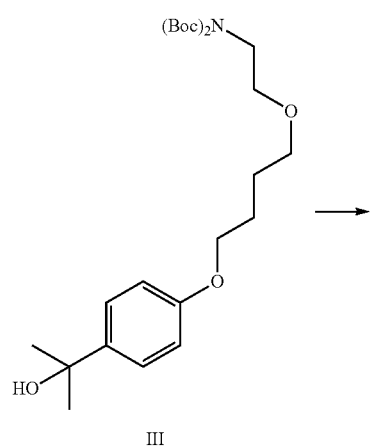

III

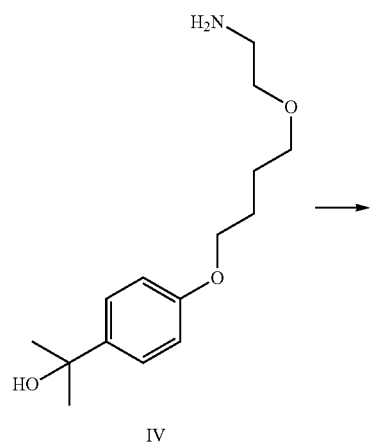

IV

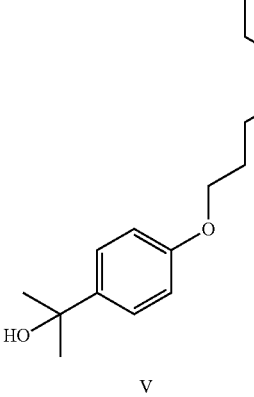

V where
- I is 1-bromo-4-(4-bromobutoxy)benzene
- II is di-tert-butoxycarbonyl(2-(4-(4-bromophenoxy)butoxy)ethyl)amine
- III is di-tert-butoxycarbonyl(2-(4-(4-(1-hydroxy-1-methylethyl)phenoxy)butoxy)ethyl)amine
- IV is 4-2-(4-(4-(2-aminoethoxy)butoxy)phenyl)propan-2-ol; and
- V is N-(2-(4-(4-(2-hydroxypropan-2-yl)phenoxy)butoxy)ethyl)methacrylamide.

Carbamate (Cbz) protecting groups are used commonly in amino acid and peptide chemistry (Greene's Protecting Groups in Organic Synthesis, 4$^{th}$ Edition, pp. 706-771). Typically, in normal protective group chemistry, installation and removal of the protective group is orthogonal (or non-conflicting) with other functional and protective groups in the molecule, and relatively harsh reaction conditions can be used during the cleavage reaction.

Linkers for use in the HPMA-Cbz copolymers have optimized controlled release properties in aqueous solution. In general, this requires much more acid-labile carbamates than those described in the prior art. The protective groups 1-(3,5-di-t-butylphenyl)-1-methylethyl carbamate (t-Bumeoc-NR$_2$; W. Voelter and J. Mueller, Liebigs Ann. Chem., 1983, 248-260) and p-methoxypheny carbamate (Moz-NR$_2$) are the most acid-sensitive carbamates used commonly in peptide chemistry, however these groups still require relatively harsh conditions to obtain rapid release of the amine [acetic acid:formic acid:water, 7:1:2; 167 minutes, room temperature, for t-Bumeoc-NR$_2$), so they are less preferred as components of controlled release linkers in buffered aqueous solutions at physiologically relevant pH. Thus, any monomer (or polymer composed therefrom) preferably releases the bound drug at significantly greater rates than the benzyl carbamates described to date.

A schematicized structure for a HPMA-Cbz-therapeutic agent copolymer according to the invention is shown below. Also shown are two different polymers differing in the repeated structure.

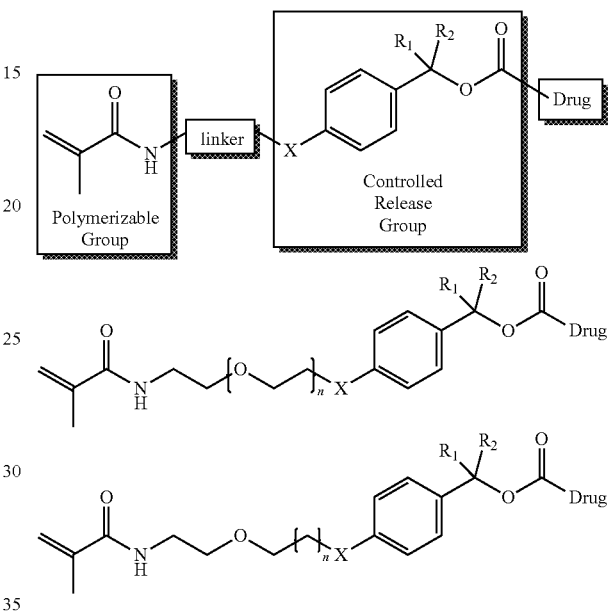

The polymerizable group is synthesized from a polymerizable starting component, e.g., a vinyl monomer, which can be copolymerized directly with other vinyl monomers to obtain a polymers conjugate as shown above. In addition to a HPMA copolymer and its derivatives, polymerizable groups can include polyethylene glycol (including branched or block copolymers, which may be degradable via peptide sequences, ester or disulfide bonds, etc.), polyglutamic acid, polyaspartic acid, dextran, chitosan, cellulose and its derivatives, starch, gelatin, hyaluronic acid and its derivatives, polymer or copolymers of the following monomers: N-isopropylacrylamide, acrylamide, N,N-dimethylacrylamide, N-vinylpyrrolidone, vinyl acetate (resulting polymer hydrolyzed into polyvinyl alcohol or PVA), 2-methacryloxyethyl glucoside, acrylic acid, methacrylic, vinyl phosphonic acid, styrene sulfonic acid, maleic acid, 2-methacrylloxyethyltrimethylammonium chloride, methacrylamidopropyltrimethyl-ammonium chloride, methacryloylcholine methyl sulfate, N-methylolacrylamide, 2-hydroxy-3-methacryloxypropyltrimethyl ammonium chloride, 2-methacryloxyethyl-trimethylammonium bromide, 2-vinyl-1-methylpyridinium bromide, 4-vinyl-1-methyl-pyridinium bromide, ethyleneimine, (N-acetyl)ethyleneimine, (N-hydroxyethyl)ethyleneimine and/or allylamine. Preferably, the water-soluble polymer is biologically inert, however, optionally the polymer may have therapeutic activity (Rapp et al., Synthesis and in vivo biodisposition of [14C]-quaternary ammonium-melphalan conjugate, a potential cartilage-targeted alkylating drug, Bioconjug Chem. (2003) 14(2):500-6).

A linker is typically connected to the polymerizable group and controlled release group as shown above. Suitable linkers include, e.g., acid-labile, CBz-derived linkers $CH_2$, NH, N—$R_3$, O, S; n=0-8, $R_1$=alkyl, $R_2$=alkyl, $R_3$=acetyl, $CH_3$.

The linker also is connected to the controlled release group, which includes the carbamate moiety. The carbamate moiety is connected to a nitrogen molecule in the drug.

A drug can be, e.g., a Janus kinase inhibitor, also known as a JAK inhibitors or jakinibs,[1] which inhibit the activity of one or more of the Janus kinase family of enzymes (JAK1, JAK2, JAK3, TYK2), thereby interfering with the JAK-STAT signaling pathway.

Polymeric forms of a HPMA-CBz-baricitinib molecule are shown below:

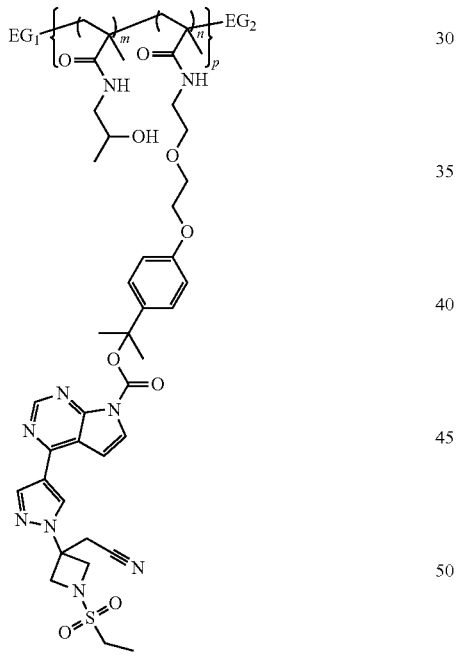

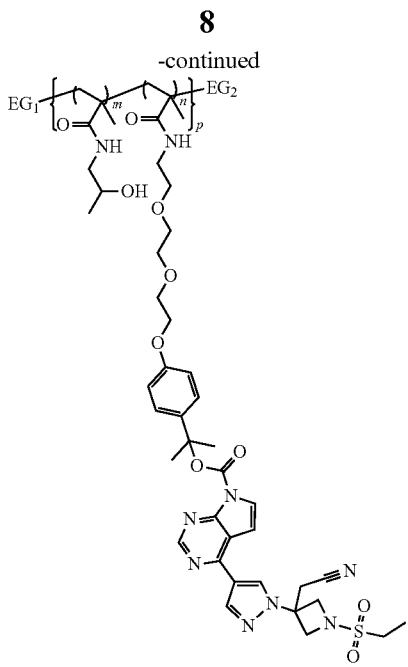

EG = End Group
Each polymer comprises a series of p units in which m and n are varied randomly In various embodiments, p, m and n are 1, 10, 20, 25, 50, 75, 100, 125, 150, 175. 200, 250 or 500.

A baracitinib-containing compound according to the invention is shown below, where X, n, R1, R2 are as described above:

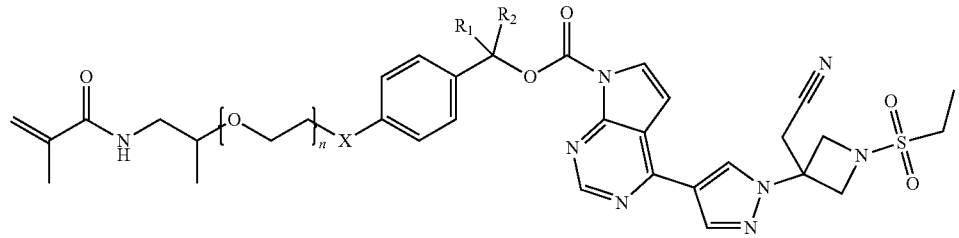

Pharmaceutical Composition Including HPMA-Cbz-Drug Copolymers

Also provided are pharmaceutical compositions that include the HPMA-Cbz-Drug copolymers.

The term "pharmaceutical composition" is defined herein to refer to a mixture or solution containing at least one therapeutic agent to be administered to a subject, e.g., a mammal or human, in order to prevent or treat a particular disease or condition affecting the mammal.

The term "pharmaceutically acceptable" is defined herein to refer to those compounds, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio. A "pharmaceutically acceptable salt", as used herein, unless otherwise indicated, includes salts of acidic and basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmaceutically acceptable anions, such as the acetate, benzoate, bromide, chloride, citrate, fumarate, hydrobromide, hydrochloride, iodide, lactate, maleate, mandelate, nitrate, oxalate, salicylate, succinate, and tartrate salts. Unless otherwise specified, the therapeutic agents used in the inventive methods are administered in free form or as a pharmaceutically salt.

Pharmaceutically acceptable base addition salts and acid addition salts are known in the art (see, for example, Berge et al., "Pharmaceutical Salts," J of Pharma Sci., 1977, 66:1-19; Remington's Pharmaceutical Sciences, 18th Ed. (1990, Mack Publishing Co., Easton, P. A.); and Goodman and Gilman's, The Pharmacological Basis of Therapeutics (10th ed. 2001)).

An HPLA-Cbz drug copolymer can be administered as a prodrug The term "prodrug" indicates a therapeutic agent that is prepared in an inactive form that is converted to an active form (i.e., drug) within the body or cells thereof by the action of endogenous enzymes or other chemicals and/or conditions.

In addition, currently available protein and peptide drugs and orally available low molecular weight drug may also benefit from the principles illustrated in the invention. For the protein or peptide drugs, they must survive this period of time against hepatic and renal clearance. Protein or peptide drugs may be stabilized by additional methods known in the art, for example, PEGylation of the protein and/or modification of the polymer backbone may provide a beneficial means in solving this problem (Smolen and Steiner, Therapeutic strategies for rheumatoid arthritis. Nature Review Drug Discovery (2003) 2:473-488).

The Cbz-containing compounds disclosed herein can also be used for imaging applications when linked to a moiety that facilitates their detection. Using modern MR imaging techniques, the specific accumulation of macromolecules can be observed in arthritic joints in the rat model of adjuvant-induced arthritis. Macromolecular imaging agents (polymeric delivery systems conjugated with near IR dyes, MRI, CT PET, gamma-scintigraphy imaging agents) can be powerful imaging and evaluation tools for inflammatory diseases, such as rheumatoid arthritis. The use of the macromolecular imaging agents also demonstrates the utility of the delivery system for the purpose of targeting a drug, which is a beneficial improvement over current treatments, for example, for treating rheumatoid arthritis. The invention provides the ability to increase the therapeutic potential and dosing window of the drugs by reducing their side effects. Furthermore, the invention may have a longer half-life in blood circulation when compared to low molecular weight drugs, which may increase the bioavailability of the drug. In addition, the invention may be used to render a hydrophobic drug hydrophilic and, particularly for peptide-based drugs, reduce immunogenecity.

The invention may, optionally, include one or more targeting moieties, which may be used to direct the delivery system to a specific tissue, such as bone, cartilage, or certain cell types, etc. Illustrative examples of targeting moieties include, but are not limited to, folic acid, mannose, bisphosphonates, quaternary ammonium groups, peptides (e.g., oligo-Asp or oligo-Glu), aminosalicylic acid, and/or antibodies or fragments or derivatives thereof (e.g., Fab, humanized antibodies, and/or single chain variable fragment (scFv)). A targeting moiety may be linked to the polymer backbone via covalent or physical bonds (linkages). Optionally, the spacers between a targeting moiety and the polymer backbone may be cleaved upon a stimulus including, but not limited to, changes in pH, presence of a specific enzyme activity (for example, cathepsins (e.g., cathepsin K), MMPs, etc.), changes in oxygen levels, etc.

Optionally, the spacers between the therapeutic agent and the polymer backbone may be cleaved upon a stimulus including, but not limited to, changes in pH, presence of a specific enzyme activity (for example, cathepsins (e.g., cathepsin K), MMPs, etc.), changes in oxygen levels, etc.

Optionally, a bio-assay label/imaging agent (or labels) is attached to the polymer backbone. It may be any label known in the art, including, but not limited to, an optical imaging agent, fluorescent probe, MRI contrast agent, radioisotope, biotin, gold, etc. Their average mol percentage per polymer chain may range from 0% to about 50%.

The bio-assay label, therapeutic agent, and/or targeting moiety may be linked to the water-soluble polymer backbone by way of a spacer. Spacers are known in the art and the person of ordinary skill in the art may select a spacer based on length, reactivity, flexibility and the like. For example, a spacer may be an alkyl or alkyne having from one to 50, preferably one to 15 carbons.

A spacer of the invention may be a peptide sequence (for example, selected from all nature amino acids) having from one to 20, preferably one to 10 residues. In yet another example, a spacer may contain a hydrazone bond which is cleavable under acidic pH. These spacers may be cleaved upon a stimulus including, but not limited to, changes in pH, presence of a specific enzyme activity (for example, cathepsins (e.g., cathepsin K), MMPs, etc.), changes in oxygen levels, etc.

Optionally, the biodegradable cross-linkage may cross-link, to a certain degree, the linear polymer backbone. The resulting delivery system still retains its water-solubility. The linkage itself is preferably cleavable under physiological conditions.

As will be appreciated by a person of ordinary skill in the art, each class (e.g., therapeutic agent, targeting moiety, bio-assays label and/or imaging agent, spacer) may comprise any number of different compounds or compositions. For example, the therapeutic agent may consist of a mixture of one or more NSAIDs and one or more JAK kinase inhibitors, such as a mixture of baricitinib and ruxolitinib.

Therefore, the invention provides the advantage that any combination of different therapeutic agents, targeting moieties, bio-assays labels, spacers and/or imaging agents may be incorporated onto the water-soluble polymer backbone. As a result, a drug delivery or imaging system can be created with two or more different therapeutic agents and/or two or more different targeting moieties and/or two or more different bio-assays labels, and/or two or more different spacers (one or more of which may be cleavable, wherein the cleavage stimulus may be different for different spacers) and/or two or more imaging agents. For example, one or more imaging agents may be combined with one or more therapeutic agents, to produce a drug/imaging agent combination, which, for example, may be used to treat and/or monitor the subject. One exemplary embodiment of such a drug/imaging agent is a method of determining the effects of a particular drug or drug combination. For example, the drug/imaging agent may contain a candidate drug wherein the imaging agent allows for enhanced monitoring of the candidate drugs effects. In another exemplary embodiment, the drug/imaging agent may also be used to treat a subject and to monitor the subject's response to the treatment.

An effective amount of a drug is well known in the art and changes due to the age, weight, severity of a subject's condition, the particular compound in use, the strength of the preparation, and the mode of administration. The determination of an effective amount is preferably left to the prudence of a treating physician, but may be determined using methods well known in the art (The Pharmacological Basis of Therapeutics, 10th ed, Gilman et al. eds., McGraw-Hill Press (2001); Remington's Pharmaceutical Science's, 18th ed. Easton: Mack Publishing Co. (1990)).

Pharmaceutical compositions comprising compounds of the invention may be prepared using methods known in the art, for example, the preparation of a pharmaceutical composition is known in the art (The Pharmacological Basis of Therapeutics, 10.sup.th ed, Gilman et al. eds., McGraw-Hill Press (2001); Remington's Pharmaceutical Science's, 18th ed. Easton: Mack Publishing Co. (1990)).

The compositions may be administered by any desirable and appropriate means. For in vivo delivery (i.e., to a subject having arthritis or other inflammatory diseases), it is preferred that the delivery system be biocompatible and preferably biodegradable and non-immunogenic. In addition, it is desirable to deliver a therapeutically effective amount of a compound in a physiologically acceptable carrier. Injection into an individual may occur subcutaneous, intravenously, intramuscularly, intraperitoneal, intraarticular or, for example, directly into a localized area. Alternatively, in vivo delivery may be accomplished by use of a syrup, an elixir, a liquid, a tablet, a pill, a time-release capsule, an aerosol, a transdermal patch, an injection, a drip, an ointment, etc.

Methods of Using HPMA-Cbz Polymers

The HPMA-Cbz-drug copolymers can be used to treat and/or prevent inflammatory conditions. The effectiveness of the copolymers in treating diseases are assessed using methods known in the art. For example when the copolymer is used to treat arthritis, methods such as those disclosed in US20090311182 can be used. Suitable animal model systems include the Adjuvant Induced Arthritis (AIA) Rat Model. In this model, male Lewis rats (175-200 g) are obtained from a commercial vendor, and allowed to acclimate for at least one week. To induce arthritis, Mycobacterium Tuberculosis H37Ra (1 mg) and N,N-dioctadecyl-N', N'-bis(2-hydroxyethyl) propanediamine (LA; 5 mg; U.S. Pat. No. 4,034,040) are mixed in paraffin oil (100 L), sonicated and s.c. injected into the base of the rat's tail (Bendele, A. M., Animal models of rheumatoid arthritis, J. Musculoskel. Neuron. Interact. (2001) 1:377-385). The rats are then randomized into 3 rats/group. The progression of the joint inflammation is followed by measuring the diameter of the ankle joint with calipers. Special care is given to the rats as the inflammation developed to ensure availability and access to water and food. The MRI contrast agents are injected directly into the jugular vein while the animal is anesthetized with Ketamine and Xylazine.

Visualization of Plasma Albumin Accumulation in RA Joints

Evans blue dye (EB, 10 mg/kg in saline) is injected into healthy and AIA rats via the tail vein. The extravasation and accumulation of dye in the areas of joint inflammation are visually observed as appearance of the blue pigment. Photographs of the ankle and paws are taken before and 8 hours after injection.

Histology

At necropsy, the major organs and limbs are removed and fixed with 10% phosphate buffered formalin for 24 hours. The organs are then dehydrated and embedded in paraffin for routine histopathological analyses. The limbs are gradually dehydrated in ascending concentrations of ethanol and embedded in poly(methyl methacrylate). Sections of the entire joint, including the undecalcified bone, were cut with a low speed saw using diamond-wafering blades. The sections were mounted on plastic slides, ground to about 50 .mu.M in thickness and surface stained using a Giemsa stain modified for plastic sections (Wang et al., Synthesis and evaluation of water-soluble polymeric bone-targeted drug delivery systems, Bioconjug. Chem. (2003) 14:853-859). The joints (knee, ankle, tarsals and metatarsals) from the same animals that are imaged by MRI are assessed for the presence of inflammation and tissue damage using the histology sections. A Bioquant histomorphometry system is used to measure the bone erosion surface.

Bone Mineral Density

The bone mineral density (BMD) of the bones in the arthritic joints is measured by peripheral dual x-ray absorptiometry (PDXA, Norland Medical Systems) adapted for small animals. For this the intact hind limbs are used and the scan region included the ankle and foot bones.

Visual and Histological Examination of AIA Rats

The development of adjuvant-induced arthritis in the rat is well described in the literature (Bendele, A. M., Animal models of rheumatoid arthritis, J. Musculoskel. Neuron. Interact. (2001) 1:377-385), and briefly summarized here. After injection of the adjuvant, changes begin to become evident about nine days later. This includes some inflammation around the eyes and enlarged and tender external genitalia. Inflammation and swelling of the front and hind limb ankle joints becomes evident at about 12 days after injection of the adjuvant.

The polymer with a drug attached is then injected into AIA rats (4/group) on day 13 after the induction of arthritis. A single dose of 10 mg/kg is given. As a control, the same dose of a low molecular weight drug is divided into four equal doses and one dose was given each day to another group of AIA rats (4/group) from day 13-16 after the induction of arthritis.

As will be recognized by a person of ordinary skill in the art, inflammation resolution drugs, anti-inflammatory drugs, anti-arthritic drugs, targeting moieties, and imaging agents, as used herein, include acceptable salts, esters, or salts of such esters. For example, glucocorticoids include pharmaceutically acceptable salts and esters thereof, therefore, when a drug is described, e.g., baricitinib, pharmaceutically acceptable salts thereof are also described, such as dexamethasone palmitate.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

EXAMPLES

The disclosure will now be illustrated with following non-limiting examples. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Example 1. Preparation of Monomers of—1-Bromo-4-(4-Bromobutoxy)Benzene

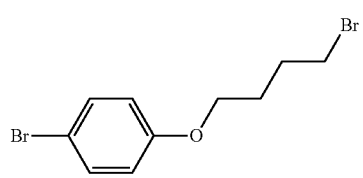

The compound is prepared according to the published method of Wang and coworkers (Bioorganic & Medicinal Chemistry Letters 2009, 19, 5965-59694) A solution of 4-bromophenol (17.1 g, 0.10 mol) in 40 mL DMF is added dropwise to a stirred mixture of 1,4-dibromobutane (43.18 g, 0.20 mol), $K_2CO_3$ (20.73 g, 0.15 mol) and DMF (100 mL) at room temperature. After the addition is complete, the reaction mixture is stirred at room temperature for 2 h and heated at 70° C. for an additional 2 h. The mixture is then cooled to room temperature, filtered, and the resulting solution is diluted with ethyl acetate (200 mL) and washed with $H_2O$ (3×200 mL). The organic layer is separated, dried over anhydrous $Na_2SO_4$, and concentrated under reduced pressure. The residue is purified by column chromatography (hexane) to give 1-bromo-4-(4-bromobutoxy)benzene as yellow oil (92.0%), which is used without further purification.

Example 2—Di-Tert-Butoxycarbonyl(2-(4-(4-Bromophenoxy)Butoxy)Ethyl)Amine

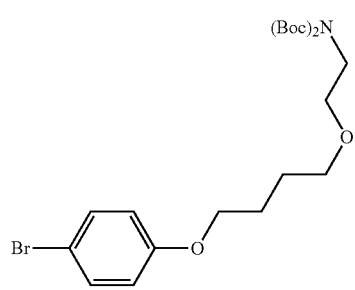

A solution of 1-bromo-4-(4-bromobutoxy)benzene (9.24 g, 0.03 mol) prepared as described in Example 1 is provided in 10 mL DMF and added dropwise to a stirred mixture of N,N-diBoc-ethanolamine (26.1 g, 0.10 mol), $K_2CO_3$ (20.73 g, 0.1 mol) and DMF (50 mL) at room temperature. After the addition is complete, the reaction mixture is stirred at room temperature for 2 h and heated at 70° C. for an additional 2 h. The mixture is cooled to room temperature, filtered, and the resulting solution is diluted with ethyl acetate (200 mL) and washed with $H_2O$ (3×200 mL). The organic layer is separated, dried over anhydrous $Na_2SO_4$, and concentrated under reduced pressure. The residue is purified by column chromatography (ethyl acetate/hexane) to give di-tert-butoxycarbonyl(2-(4-(4-bromophenoxy)butoxy)ethyl)amine.

Example 3—Di-Tert-Butoxycarbonyl(2-(4-(4-(1-Hydroxy-1-Methylethyl)Phenoxy)Butoxy)Ethyl) Amine

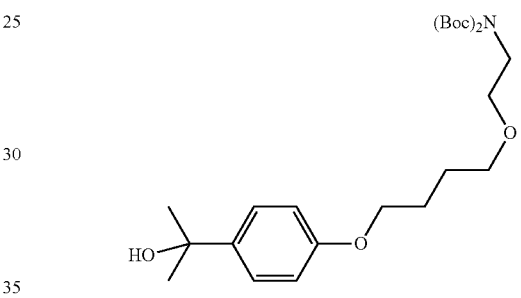

Under an atmosphere of dry nitrogen, a 250 mL round bottom two neck flask equipped with a magnetic stir bar, a septum inlet, and a reflux condenser is charged with magnesium turnings (0.535 g, 0.022 mol) and dry THF (50 mL). Approximately 1 mL of a solution of di-tert-butoxycarbonyl (2-(4-(4-bromophenoxy)butoxy)ethyl)amine (9.77 g, 0.02 mol) in 50 mL THF is added by syringe to the vigorously stirred mixture to initiate the Grignard reaction. After initiation, the remaining aryl bromide solution is added gradually (over the course of one hour) to maintain the THF solution at reflux. Once the magnesium is dissolved, the mixture is cooled to 0° C. and acetone (0.03 mol in 10 mL dry THF is added over the course of 2 minutes. One the reaction is complete, most of the solvent is removed in vacuo and the remainder is treated with aqueous ammonium chloride solution (60 mL, 1 M) and the mixture is stirred until evolution of ammonia stops. The mixture is transferred to a separatory funnel and extracted (3×100 mL) with ethyl acetate. The combined organic extracts are subsequently washed with water (2×100 mL) and brine, dried over anhydrous $NaSO_4$, and filtered. The ethyl acetate is removed under reduced pressure and the residue is purified by column chromatography (ethyl acetate/hexane) to give di-tert-butoxycarbonyl(2-(4-(4-(1-hydroxy-1-methylethyl)phenoxy) butoxy)ethyl)amine.

Example 4—2-(4-(4-(2-Aminoethoxy)Butoxy)Phenyl)Propan-2-ol

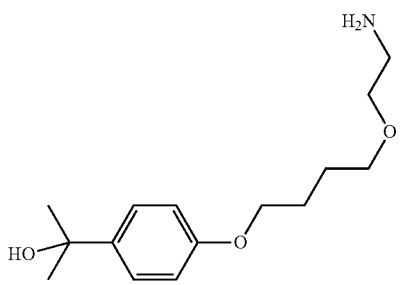 [SMILES: CC(C)(O)c1ccc(OCCCCOCCN)cc1]

Di-tert-butoxycarbonyl(2-(4-(4-(1-hydroxy-1-methylethyl)phenoxy)butoxy)ethyl)amine is suspended in 200 mL of 1 M aqueous H₂SO₄ and the mixture is allowed to stir at room temperature for 48 h. The mixture is neutralized with potassium carbonate, transferred to a separatory funnel and extracted (3×100 mL) with ethyl acetate. The combined organic extracts are subsequently washed with water (2×100 mL) and brine, dried over anhydrous NaSO₄, and filtered. The ethyl acetate is removed under reduced pressure and the residue is purified by column chromatography (ethyl acetate/hexane) to give 2-(4-(4-(2-aminoethoxy)butoxy)phenyl)propan-2-ol.

Example 5—N-(2-(4-(4-(2-Hydroxypropan-2-yl)Phenoxy)Butoxy)Ethyl)Methacrylamide

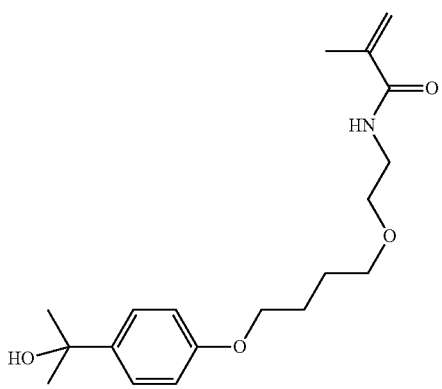 [SMILES: C=C(C)C(=O)NCCOCCCCOc1ccc(C(C)(C)O)cc1]

Under an atmosphere of dry nitrogen, 2-(4-(4-(2-aminoethoxy)butoxy)phenyl)propan-2-ol (2.67 g, 0.01 mol) is dissolved in anhydrous methylene chloride (20 mL) containing anhydrous pyridine (0.87 mL, 0.012 mol) and methacryloyl chloride (0.96 mL, 0.01 mol) dissolved in 10 mL of CH₂Cl₂ is added dropwise. After 1 h the mixture is transferred to a separatory funnel and extracted with acetate buffer (2×100 mL) to remove the pyridine, washed with water and brine, and dried over anhydrous NaSO₄. The solution is filtered to remove the drying agent and the solvent is removed by rotary evaporation. Purification is performed by column chromatography on silica (hexane/ethyl acetate) to yield N-(2-(4-(4-(2-hydroxypropan-2-yl)phenoxy)butoxy)ethyl)methacrylamide.

Example 6—(4-Bromobutyl)(4-Bromophenyl)Sulfane

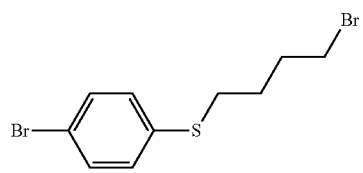

This compound is prepared according to the method described in Example 1. Under rigorous oxygen free conditions, a solution of 4-bromothiophenol (18.8 g, 0.10 mol) in 40 mL DMF is added dropwise to a stirred mixture of 1,4-dibromobutane (43.18 g, 0.20 mol), K₂CO₃ (20.73 g, 0.15 mol) and DMF (100 mL) at room temperature. After the addition is complete, the reaction mixture is stirred at room temperature for 2 h. The mixture is cooled to room temperature, filtered, and the resulting solution was diluted with ethyl acetate (200 mL) and washed with H₂O (3×200 mL). The organic layer was separated, dried over anhydrous Na₂SO₄, and concentrated under reduced pressure. The residue is purified by column chromatography (hexane) to give (4-bromobutyl)(4-bromophenyl)sulfane, which is used without further purification.

Example 7—N-(2-(4-04-(2-Hydroxypropan-2-yl)Phenyl)Thio)Butoxy)Ethyl)Methacrylamide

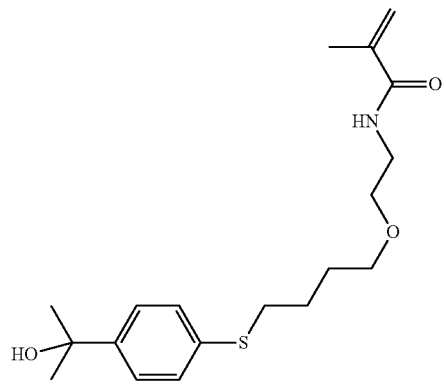

The title compound is prepared from (4-bromobutyl)(4-bromophenyl)sulfane using the procedures outline in Examples 2-5.

Example 8—4-Bromo-N-(4-Bromonhenyl)Butanamide

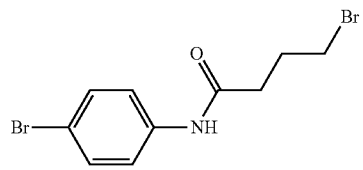 [SMILES: O=C(CCCBr)Nc1ccc(Br)cc1]

The title compound is prepared using the method of C. Beinat and coworkers (Bioorg. Med. Chem. Lett. 22 (2012) 2380-2384.). Briefly, the appropriate ω-bromoalkanoic acid (1 mmol) is suspended in oxalyl chloride (ca. 2 mL), stirred at ambient temperature for 45 min, and the excess oxalyl chloride evaporated under reduced pressure. The residue is dissolved in $CH_2Cl_2$ (10 mL), cooled to −78° C., and treated dropwise with a solution of 4-bromoaniline (1.1 mmol) and Et 3 N (1.1 mmol) in $CH_2Cl_2$ (11 mL). The mixture is warmed to ambient temperature, stirred for 1 h, and $CH_2Cl_2$ (50 mL) is added. The solution is washed with $H_2O$ (50 mL), 1 M aq. HCl (50 mL), sat. aq. $Na_2CO_3$ (50 mL), brine (50 mL), dried ($Na_2SO_4$), and the solvent evaporated under reduced pressure to give the crude amide in 54-94% over 2 steps.

Example 9—6-Bromo-N-(4-Bromophenyl)Hexanamide

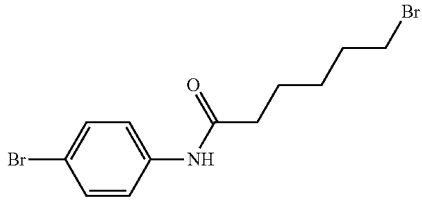 [SMILES: O=C(CCCCCBr)Nc1ccc(Br)cc1]

The title compound is prepared using the method described in Example 8.

Example 10 Tert-Butyl (4-Bromobutanoyl)(4-Bromophenyl)Carbamate

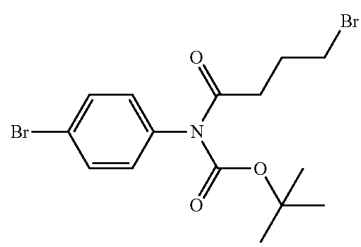 [SMILES: CC(C)(C)OC(=O)N(C(=O)CCCBr)c1ccc(Br)cc1]

4-Bromo-N-(4-bromophenyl)butanamide (3.2 g, 0.01 mol) and Boc anhydride (5 grams) are placed in a a round bottomed flask and the mixture is heated (neat) at 40° C. for 24 h. The excess Boc anhydride is removed in vacuo and the residue is purified by column chromatography (ethyl acetate/hexane) to give the title compound.

Example 11—Tert-Butyl (6-Bromohexanoyl)(4-Bromophenyl)Carbamate

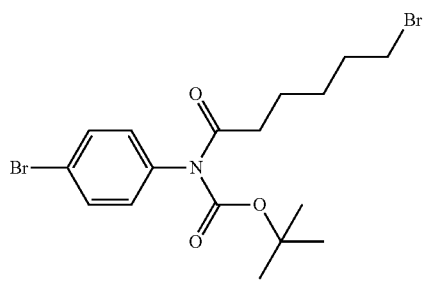 [SMILES: CC(C)(C)OC(=O)N(C(=O)CCCCCBr)c1ccc(Br)cc1]

The title compound is prepared using the method described in Example 10.

Example 12—N-(4-(2-Hydroxypropan-2-yl)Phenyl)-4-(2-Methacrylamidoethoxy)Butanamide

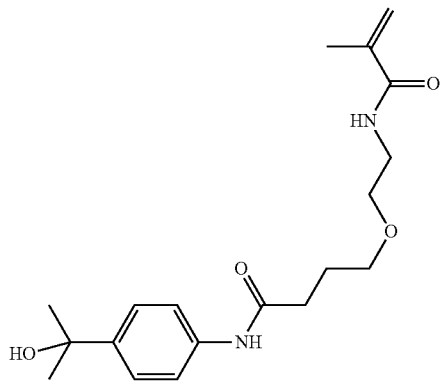 [SMILES: C=C(C)C(=O)NCCOCCCC(=O)Nc1ccc(C(C)(C)O)cc1]

The title compound is prepared from tert-butyl (4-bromobutanoyl)(4-bromophenyl)carbamate using the procedures outline in examples 2-5.

Example 13—General Procedure for Introduction of PEG Spacers

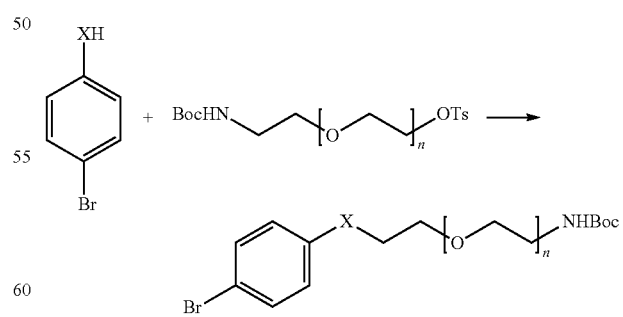

The general procedure for introduction of the PEG spacers is adapted from Christiansen and coworkers (J. Med. Chem. 2016, 59, 4849-4858). A flask under nitrogen is charged with either 4-bromophenol or 4-bromothiophenol (2 mmol), $K_2CO_3$ (6 mmol), and 2-(2-(N-(Boc)amino)ethoxy)

ethyl tosylate (4 mmol) dissolved in MeCN (50 mL), and the mixture is heated at reflux for 24 h. The reaction is cooled to rt, diluted with water, and extracted with EtOAc (×3). The organic phases are combined, washed with brine, dried over Na₂SO₄, and concentrated in vacuo. The residue is purified by flash chromatography (SiO₂, EtOAc:petroleum ether, 1:2) to provide the title compounds.

Example 14—General Procedure for Introduction of PEG Spacers

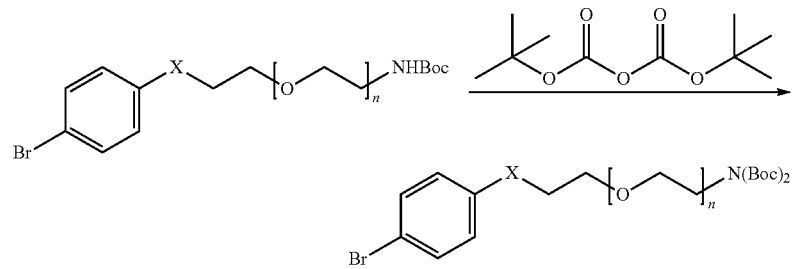

Di-Boc protection was performed using the method outlined in Example 10.

Example 15—General Procedure for Preparation of Monomers Featuring PEG Spacers

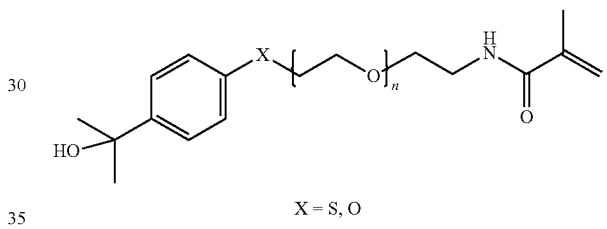

X = S, O

The methylmethacrylate monomers are prepared from the di-Boc derivatives (Example 14) by the methods outlined in Examples 2-5.

Example 16—General Procedure for Preparation of Phenyl Carbonates

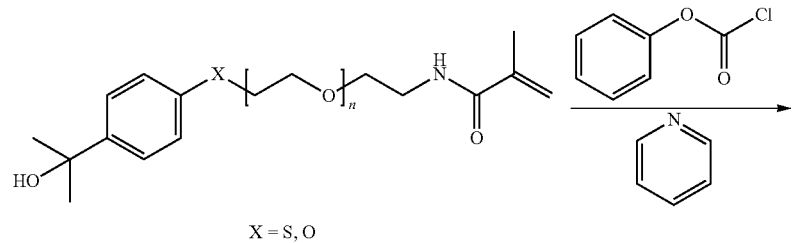

X = S, O

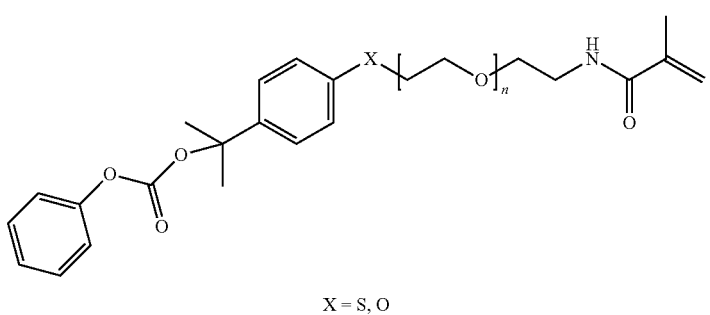

X = S, O

The general procedure to form activated carbonates is adopted from Voelter et al. (Liebigs Ann. Chem. 1983, 248-260). To a chilled (−5° C.) solution containing the appropriate monomer (20 mmol) and pyridine (2.36 g, 30 mmol) in 35 mL of anhydrous methylene chloride, phenyl chloroformate (3.3 g, 21 mmol) in 20 ml CH$_2$Cl$_2$ is added over the course of 1 h. The solution is stirred for 15 h, during which time the amount of precipitate increases. The reaction mixture is poured over ice, 50 mL of additional CH$_2$Cl$_2$ is added, and the organic phase is separated. The organic phase is washed (5×50 mL) with water, dried over Na$_2$SO$_4$, and evaporated to yield a solid which is recrystallized from MTBE.

Example 17—General Procedure for Preparation of P-Nitrophenyl Carbonates

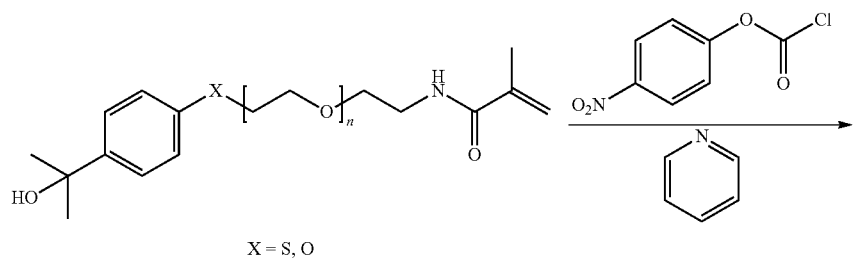

X = S, O

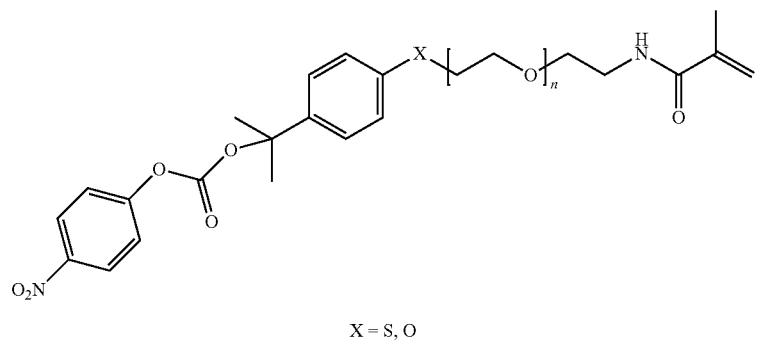

X = S, O

The general procedure for forming activated carbonates is adopted from Voelter et al. (Liebigs Ann. Chem. 1983, 248-260). To a chilled (−5° C.) solution containing the appropriate monomer (20 mmol) and pyridine (2.36 g, 30 mmol) in 35 mL of anhydrous methylene chloride, 4-nitrophenyl chloroformate (4.23 g, 21 mmol) in 20 ml CH$_2$Cl$_2$ is added over the course of 1 h. The solution is stirred for 15 h, during which time the amount of precipitate increased. The reaction mixture is poured over ice, 50 mL of additional CH$_2$Cl$_2$ is added, and the organic phase is separated. The organic phase is washed (5×50 mL) with water, dried over Na$_2$SO$_4$, and evaporated to yield a solid, which is used without further purification.

Example 18—General Procedure for Preparation of Fluoroformates

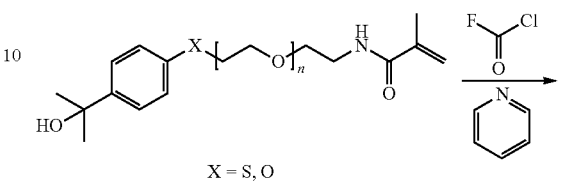

X = S, O

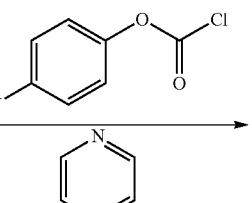

-continued

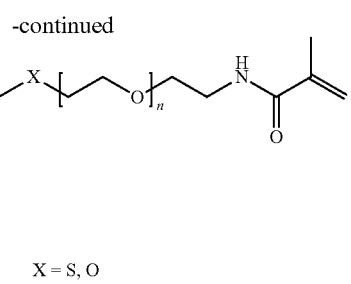

X = S, O

The general procedure to form the activated carbonates is adopted from Voelter et al. (Liebigs Ann. Chem. 1983, 248-260).

Example 19—General Procedure for Loading the Monomers

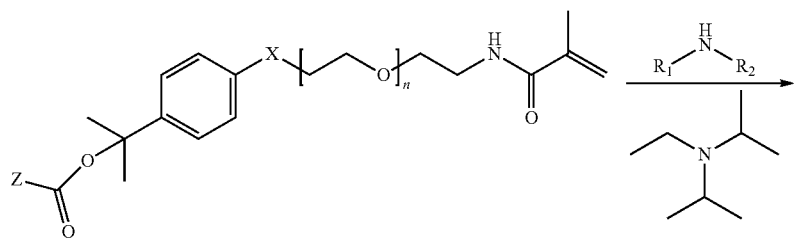

X = S, O
Z = F, Ph—O, 4-NO$_2$PhO

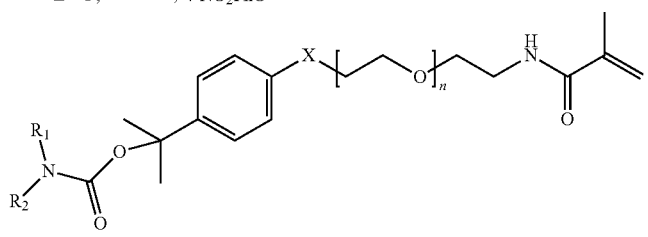

X = S, O
Z = F, Ph—O, 4-NO$_2$PhO

The activated carbonate or fluoroformate (10 mmol) is dissolved in 50 mL of anhydrous THF containing diisopropylethyl amine (12 mmol) and the solution is cooled to 0° C. The primary or secondary amine containing drug molecule (10 mmol) is added in 10 mL of dry THF and the mixture is stirred 8 h at 0° C. and a further 16 h at room temperature. The THF is evaporated under reduced pressure, and the remainder is dissolved in CH$_2$Cl$_2$ (200 mL) and washed with acetate buffer (3×100 mL, pH=4.5, 0.1 M). The organic layer is dried over Na$_2$SO$_4$, and evaporated to yield the drug loaded monomer, which is purified by silica gel flash chromatography.

I claim:

1. A compound represented by one of the following formulae:

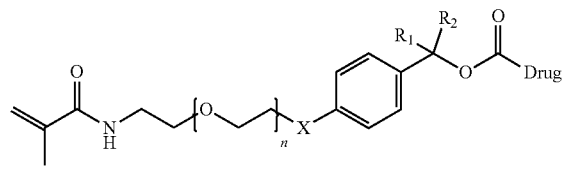

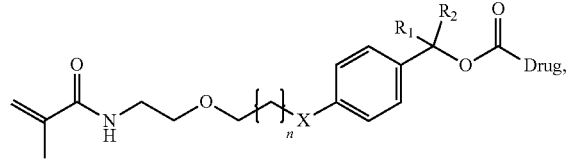

or a pharmaceutically acceptable salt thereof,
wherein:
X is CH$_2$, NH, N—R$_3$, N(H)C(O), O, or S;
n is 0-8;
R$_1$ is alkyl;
R$_2$ is alkyl; and
R$_3$ is acetyl or CH$_3$.

2. The compound of claim 1, wherein Drug is a janus kinase inhibitor.

3. The compound of claim 1, wherein Drug is baricitinib, ruxolitinib, tofacitinib, oclacitinib, upadacitinib, or peficitinib.

4. The compound of claim 3, wherein Drug is baricitinib.

5. The compound of claim 1, wherein the compound is represented by:

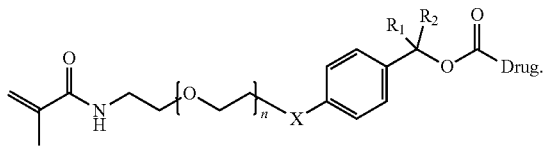

6. The compound of claim 1, wherein the compound is represented by:

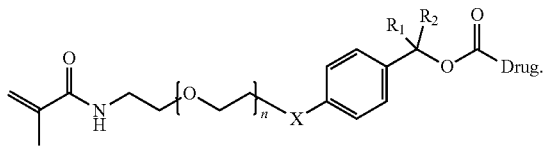

7. The compound of claim 1, wherein X is O or S.
8. The compound of claim 1, wherein X is N(H)C(O).
9. The compound of claim 1, wherein R$^1$ is CH$_3$.
10. The compound of claim 1, wherein R$^2$ is CH$_3$.
11. The compound of claim 1, wherein n is 3.
12. The compound of claim 1, wherein n is 2.
13. The compound of claim 1, wherein n is 1.

14. The compound of claim 1, wherein the compound is
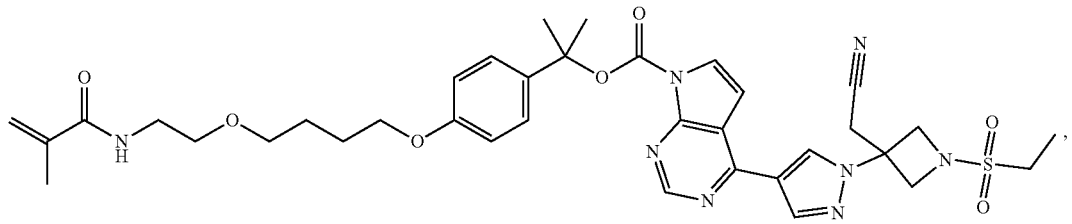 [SMILES: C=C(C)C(=O)NCCOCCCCOc1ccc(C(C)(C)OC(=O)n2ccc3c(-c4cnn(C5(CC#N)CN(S(=O)(=O)CC)C5)c4)ncnc32)cc1]
or a pharmaceutically acceptable salt thereof.
15. The compound of claim 1, wherein the compound is
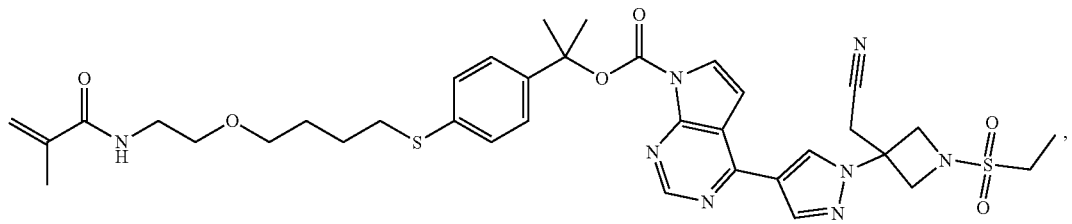
or a pharmaceutically acceptable salt thereof.
16. A compound that is
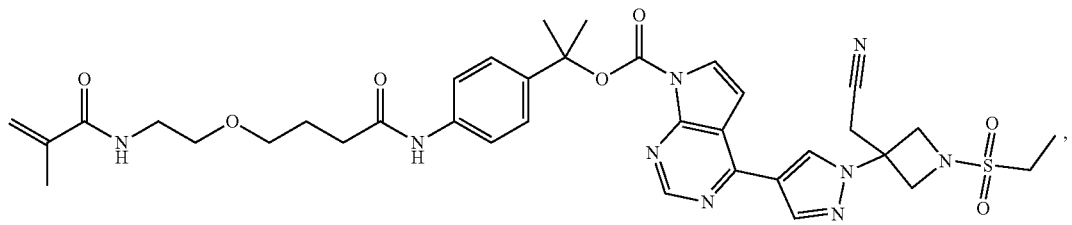 [SMILES: C=C(C)C(=O)NCCOCCCC(=O)Nc1ccc(C(C)(C)OC(=O)n2ccc3c(-c4cnn(C5(CC#N)CN(S(=O)(=O)CC)C5)c4)ncnc32)cc1]
or a pharmaceutically acceptable salt thereof.
17. The compound of claim 1, wherein the compound is
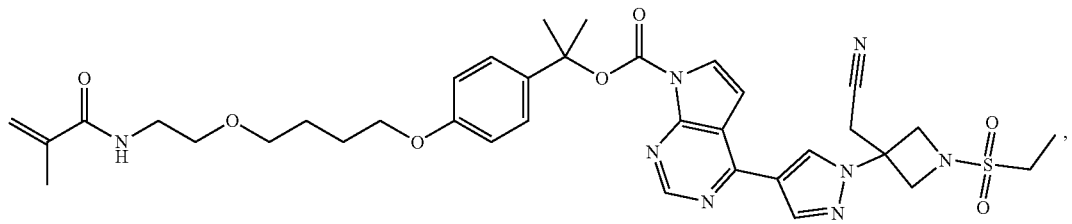 [SMILES: C=C(C)C(=O)NCCOCCCCOc1ccc(C(C)(C)OC(=O)n2ccc3c(-c4cnn(C5(CC#N)CN(S(=O)(=O)CC)C5)c4)ncnc32)cc1]
or a pharmaceutically acceptable salt thereof.

18. A compound that is
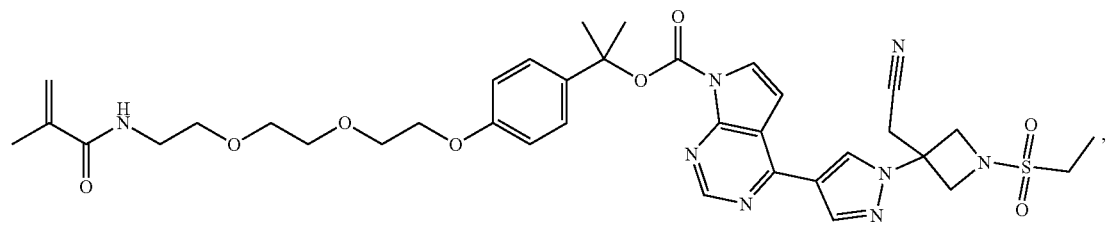 [SMILES: C=C(C)C(=O)NCCOCCOCCOc1ccc(C(C)(C)OC(=O)n2ccc3c(-c4cnn(C5(CC#N)CN(S(=O)(=O)CC)C5)c4)ncnc32)cc1]
or a pharmaceutically acceptable salt thereof.